United States Patent
Shechtman et al.

(10) Patent No.: US 6,524,260 B2
(45) Date of Patent: *Feb. 25, 2003

(54) CONTOUR MAPPING SYSTEM AND METHOD PARTICULARLY USEFUL AS A SPINE ANALYZER AND PROBE THEREFOR

(75) Inventors: Adi Shechtman, Nofit (IL); Gideon E. Sturlesi, Bikat Beit Hakerem (IL); Florin Coter, Haifa (IL)

(73) Assignee: Ortho Scan Technologies Inc., Sherborn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/035,446

(22) Filed: Jan. 4, 2002

(65) Prior Publication Data

US 2002/0133098 A1 Sep. 19, 2002

Related U.S. Application Data

(63) Continuation-in-part of application No. 09/810,538, filed on Mar. 19, 2001.
(60) Provisional application No. 60/316,249, filed on Sep. 4, 2001, provisional application No. 60/276,480, filed on Mar. 19, 2001, and provisional application No. 60/276,478, filed on Mar. 19, 2001.

(51) Int. Cl.$^7$ .............................................. A61B 51/03
(52) U.S. Cl. .................... 600/594; 600/587; 600/409
(58) Field of Search ................................ 600/594, 587, 600/409

(56) References Cited

U.S. PATENT DOCUMENTS

| | | | | |
|---|---|---|---|---|
| 5,042,505 A | * | 8/1991 | Mayer et al. | 600/594 |
| 5,181,525 A | * | 1/1993 | Bunnell | 600/594 |
| 5,303,480 A | * | 4/1994 | Chek | 600/587 |
| 6,312,392 B1 | * | 11/2001 | Herzon | 600/587 |

FOREIGN PATENT DOCUMENTS

| | | | | |
|---|---|---|---|---|
| DE | 4216458 A1 | * | 12/1993 | A61B/5/103 |
| DE | 4402562 A1 | * | 8/1995 | A61B/5/103 |

* cited by examiner

Primary Examiner—Robin O. Evans
(74) Attorney, Agent, or Firm—G. E. Ehrlich Ltd.

(57) ABSTRACT

A contour mapping system useful as a spine analyzer includes a probe for application to a user's hand with the outer tip of at least one finger of the hand movable along the outer surface of the person's spine or other object whose contour is to be mapped. A position sensor carried by the probe is movable with the user's finger as the finger moves along the outer surface of the object. The system tracks and displays the movements of the position sensor as the probe is moved with the user's hand along the outer surface of the object. An ultrasonic transducer may be combined with the position sensor on the same probe and used to examine particular vertebrae, such as apex vertebrae, for rotation and/or deformation.

40 Claims, 15 Drawing Sheets

Fig. 12a (Normal)

Fig. 12b (Rotated)

Fig. 12c Deformed (Not Rotated)

CONTOUR MAPPING SYSTEM AND METHOD PARTICULARLY USEFUL AS A SPINE ANALYZER AND PROBE THEREFOR

RELATED APPLICATIONS

The present application is a Continuation-in-Part of application Ser. No. 09/810,538 filed Mar. 19, 2001, and includes subjects matter of Provisional Application No. 60/276,478 filed Mar. 19, 2001, Provisional Application No. 60/276,480 filed Mar. 19, 2001, and Provisional Application No. 60/316,249, filed Sep. 4, 2001, the priority dates of which applications are claimed herein.

FIELD AND BACKGROUND OF THE INVENTION

The present invention relates to contour mapping systems and methods for mapping the contour of an object. The invention is particularly useful for mapping the curvature of the spine of a human being in order to detect spine deformities, such as scoliosis and kyphosis, and is therefore described below with respect to this application. The invention also relates to probes particularly useful in such a contour mapping system.

Scoliosis refers to a lateral spinal curve of a certain degree that affects an estimated 500,000 adults in the USA. The most common form of scoliosis, called idiopathic (i.e., of unknown origin), is so named because its real cause is unknown. There is a higher tendency for scoliosis to run in families, with many more affected girls than boys; thus adolescent girls over the age of nine are five times more likely to be diagnosed with scoliosis than boys of the same age. Early detection of scoliosis can lead to effective treatment. Currently, scoliosis is treated by special braces, surgery, or by a combination of both.

Screening for scoliosis detection has been adopted in most of the U.S. schools and in most of the Western World countries. Between 10 to 30% of the children that undergo a simple examination at school are advised to visit a pediatrician/orthopedist for a more thorough investigation and treatment recommendation. Approximately 30% of the latter are found to require long term treatment.

The basic tool for detecting scoliosis, and for quantifying its severity, is the spinal roentgenogram consisting of full length radiographs of the spine, one frontal and another sidewise. This is also the tool used by the physician during the long period of treatment and follow up.

Thus, a treated child will be exposed to a significant number of X-ray procedures, two to three double sessions per year. As a result, there is a concern about the cumulative effects of this high dose radiation. Recent publications reveal a three to four times higher risk to develop breast cancer and a number of thyroid cancers in women undergoing repetitive X-ray exposures as part of their scoliosis treatment. In spite of efforts to reduce the radiation dose, there is still a higher lifetime risk of cancer from spinal radiographs among people with adolescent idiopathic scoliosis.

Therefore, there is a real need for an alternative device, system and method capable of being used for the same diagnostic function as the X-ray today but avoiding the radiation exposure hazard, especially for young people, arising from multiple exposures during a long period of treatment. There is also a real need for a device, system and method capable of providing more detailed information about the examined spine, such as the degree of curvature of the spine, or the degree of rotation and/or deformation of any particular vertebra therein.

A number of alternative systems are described in the literature for measuring spine curvature in order to avoid the health hazard of radiation; see for example U.S. Pat. Nos. 2,324,672; 4,036,213; 4,600,012; 4,664,130; 4,760,851; 5,251,127; and 5,471,995. However, no system has yet proved to be entirely satisfactory. Efforts are therefore continually being made to develop systems, devices and methods for measuring the spinal curve in a manner which enables more precision, and which can be performed more conveniently, than the existing systems.

OBJECTS AND BRIEF SUMMARY OF THE INVENTION

An object of the present invention is to provide a novel probe, contour mapping system and method for mapping the contour of an object, paticularly a person's spine in a precise, convenient and simple manner.

Another object of the invention is to provide a novel probe, contour mapping system and method for measuring the curvature of the spine of a person in order to detect and/or treat for spine deformities, such as scoliosis or kyphosis.

According to one aspect of the present invention, there is provided a probe for use in a contour mapping system, the probe being constructed so as to be carried by a user's hand with the tip of at least one finger of the user's hand movable along the outer surface of the object whose contour is to be mapped; the probe including a position sensor to be located at a predetermined position with respect to the finger tip for sensing the position of the probe, and thereby of the finger tip, as the probe is moved by the user's hand along the outer surface of the object whose contour is to be mapped.

The user's finger or fingers are thus utilized as the "feeling part" of the probe. This not only simplifies the construction of the probe, but also exploits the sense of touch for following the curvature to be mapped. Such a system is therefore particularly useful for mapping the curvature of a person's spine, but it will be appreciated that it could be used in other applications involving the mapping of the contour of other objects.

One preferred embodiment of the invention is described wherein the probe is constructed for grasping by the user's hand with the tip of at least one finger in a predetermined position with respect to the position sensor carried by the probe. The described probe includes a handle graspable by the user's hand, and a finger supporting member fixed at one end of the handle for supporting the user's index finger at the predetermined position with respect to the position sensor. In this embodiment, the position sensor is fixed within the finger supporting member.

A second embodiment is described wherein the probe is constructed for mounting on at least one finger of the user's hand, with the position sensor at the predetermined position with respect to the finger tip. In the described embodiment, the probe is constructed for mounting on two adjacent fingers of the user's hand with the finger tips exposed for direct contact with the object whose contour is to be mapped.

According to a further embodiment, the probe may also include an ultrasonic transducer for sensing the physical structure of the object whose contour is to be mapped.

According to another aspect of the present invention, there is provided a probe for contour mapping the outer surface of an object comprising: a position sensor carried by the probe for sensing the position of the probe as it is moved along the outer surface of the object whose contour is to be mapped; and an ultrasonic transducer carried by the probe for sensing the physical structure of the object whose contour is to be mapped.

According to further aspects of the invention, there is provided a contour mapping system for mapping the contour of an object, comprising a probe of any of the above embodiments, and a position tracking system for tracking the movements of the position sensor of the probe, and thereby of the finger tip of the user's hand, as the probe is moved with the user's hand along the outer surface of the object.

In the embodiments described below, the object whose contour is to be mapped is the spine of a person, and the system includes a data processor programmed to display data regarding the person's spine as mapped by the probe. The data processor may also be programmed to compute and to display various characteristics of the mapped spine, such as the curvature of the spine, the distance between adjacent vertebrae, and/or the rotation or deformation of any particular vertebra in the spine.

According to yet another aspect of the invention, there is provided a method of examining a subject's spine, comprising: providing the hand of an examiner with a probe having a position sensor at a predetermined location with respect to a finger tip of the examiner's hand; moving the finger tip along the spinous processes of the vertebrae of the subject's spine; upon feeling a spinous process with the finger tip, recording the position of the probe, and thereby of the felt spinous process; and utilizing the recorded positions of the felt spinous processes to calculate and display the curvature of the subject's spine.

According to a still further aspect of the invention, there is provided a method of examining a subject's spine, comprising: moving a position sensor along the outer surface of the subject's spine to map the subject's spine curvature; and utilizing an ultrasonic transducer to examine the physical structure of at least one vertebra of the subject's spine to detect deformation and/or rotation of the examined vertebra.

According to further features in one preferred embodiment of the invention described below with respect to this aspect, the position sensor maps the subject's spine curvature by sensing the spinous processes of the vertebrae in the subject's spine, and the ultrasonic transducer examines the physical structure of at least one vertebra by sensing and displaying the location and contour of the two transverse processes relative to each other and to the spinous process of the examined vertebra such as to provide an indication of the rotation and/or deformation of the examined vertebra.

As will be described more particularly below, such a probe, system and method may be used for examining the spine of a subject and for providing detailed information about the examined spine without subjecting the subject to the hazards of radiation.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
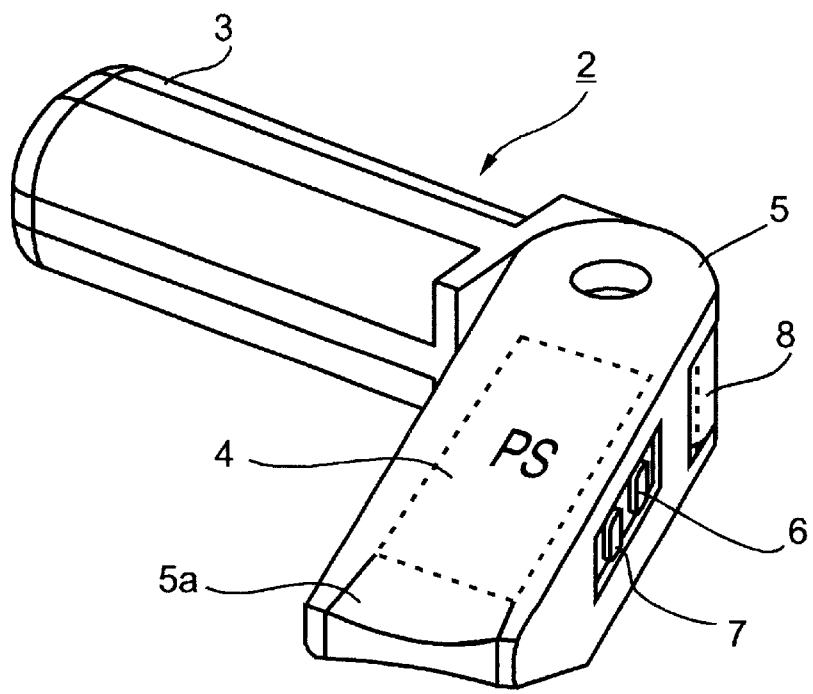
FIG. 1 is a three-dimensional view illustrating one form of probe constructed in accordance with the present invention.
Figure 2:
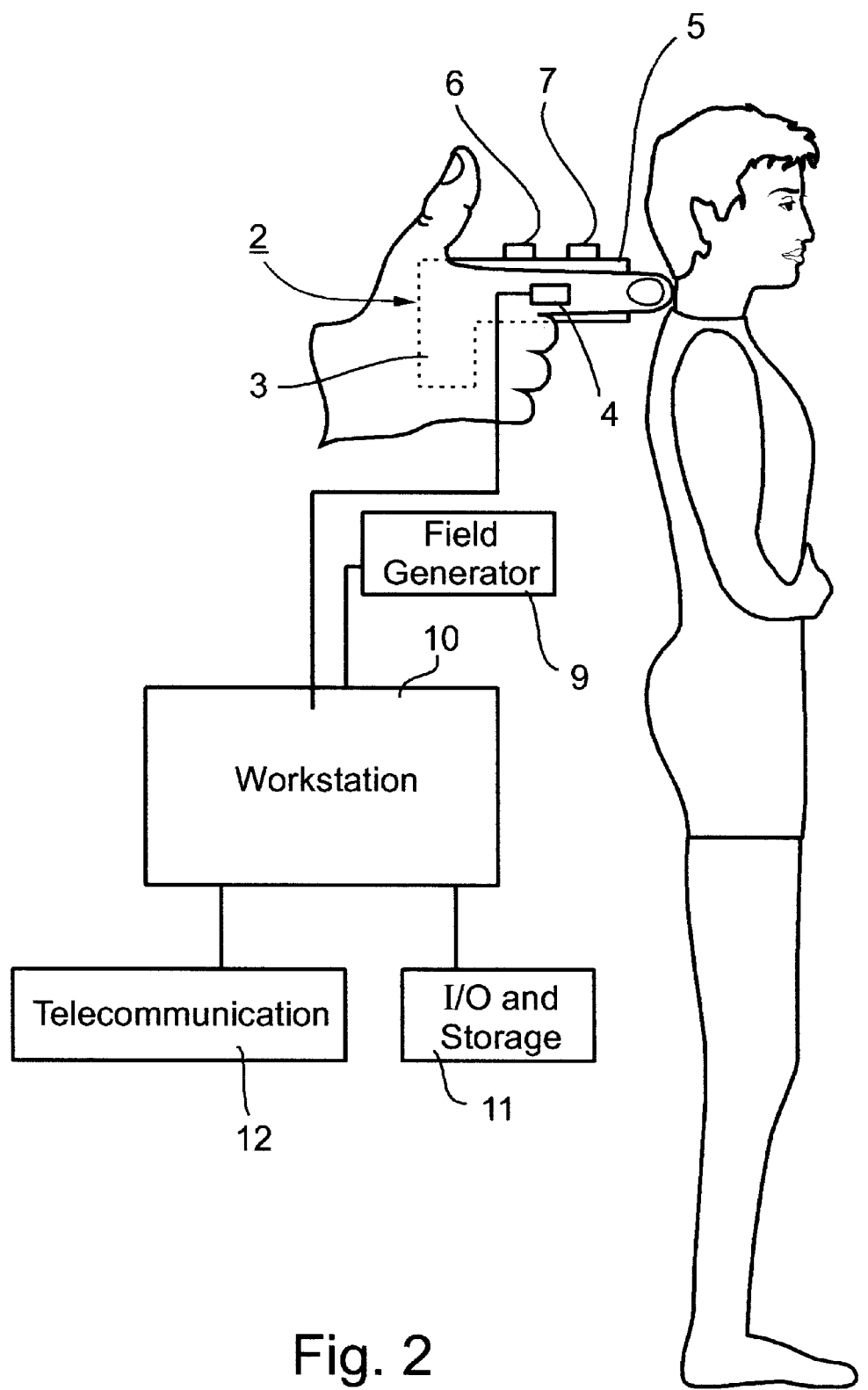
FIG. 2 illustrates the use of the probe of FIG. 1 in a computerized spine analyzer system for measuring the curvature or other characteristics of the spine of a person.

FIG. 1 illustrates one form of probe, therein generally designated 2, to be carried by a user's hand and to be used in the manner shown in FIG. 2 for mapping the curvature of a person's spine, e.g., in order to detect the presence and severity of a deformation in the spine, such as scoliosis or kyphosis. As will be described more particularly below and as shown in FIG. 2, the probe 2 is constructed such that when it is grasped by a user's hand, the outer tip of the index finger of the user's hand is at a predetermined position with respect to a position sensor carried by the probe. That is, the sensor is fixed at a known position with respect to the user's index finger tip; such position is predetermined for each user according to the finger size. As the finger tip is moved along the outer surface of the subject's spine, the movements of the position sensor will thus trace or map the curvature of the spine.

Probe 2 illustrated in FIG. 1 includes a handle 3 graspable by the hand of the user, and a position sensor 4 for use in tracking the movements of the probe. Position sensor 4 is carried by a finger-supporting member 5 extending substantially perpendicularly from one end of the handle 3 and formed with a groove 5a for receiving the index finger of the user's hand grasping the handle 3. The finger-supporting member 5 is of a length less than the length of the user's index finger so that when the user grasps the handle 3 with the user's index finger within groove 5a, the outer tip of the user's index finger is exposed for contact with the outer surface of the spine whose curvature is to be mapped, as shown in FIG. 2.

A person's spine is composed of 33 vertebrae. A typical vertebra consists of two main parts: an inner, ventral part called the body; and an outer, dorsal part called the vertebral arch. These two parts surround a central space through which the spinal cord passes.

The vertebral arch consists of seven bony outgrowths as follows: two pedicles that project backwardly from the body; two laminae which form connecting processes between the pedicles; the spinous process, which is a bony outgrowth that projects backwardly and downwardly; and two transverse processes, which project laterally and provide sites for the attachment of muscles and ligaments.

As will be described more particularly below, the spinal curve is sensed in the described preferred embodiments by finger tip sensing the spinous process of each vertebra.

Probe 2 further includes a button 6 depressible by the thumb of the user's hand to enter into the position tracking system the location of the position sensor 4 at the instant the button is depressed. Probe 2 includes a second button 7, next to button 6, and also depressible by the thumb of the user. Button 7 may be used for canceling a previous entry, or for canceling all the previous entries. For example, the tracking system can be programmed such that a short depression of button 7 cancels the previous entry, whereas a long depression of the button clears the system of all the previous entries for the respective operation. The probe may also include an audible or visual signaling device 8 (FIG. 1) for providing an appropriate signal to indicate a reading has been properly entered.

When probe 2 is used, as shown in FIG. 2, for mapping the curvature of a person's spine, the movements of the position sensor 4, which correspond to the movements of the user's index finger and thereby of the curvature of the person's spine, are tracked by a position tracking system included within a data processor in a workstation 10. Many position tracking systems are known in the prior art for the determination of the position of an object in a three-dimensional space. Such systems, once calibrated and normalized, track the movements of the object to thereby determine its actual position at all times. Thus, position tracking systems are known which include mechanical, acoustical, radio-frequency, magnetic, electromagnetic and optical devices for tracking the movements of the object. Examples of such position tracking systems based on acoustical or electromagnetic fields are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which patents are incorporated herein by reference.

In the preferred embodiment of the invention illustrated in FIG. 2, the position tracking system is of the electromagnetic field type. It includes a field generator 9 for generating and transmitting a magnetic field in the space occupied by the person's spine to be mapped. The position sensor 4 within the probe 2 is a 6-D magnetic sensor for sensing the instantaneous position of the probe within the generated magnetic field. Both the field generator 9 and the position sensor 4 produce signals which are applied to the workstation 10. The workstation tracks the movement of the position sensor 4, and thereby of the probe 2, as the probe is moved with the user's hand along the outer surface of the subject's spine.

The tracked positions as determined by the workstation 10 are recorded in an input/output storage device 11 for further processing, as will be described more particularly below. In addition, the output of the workstation can be transmitted via a telecommunication device 12 to a remote location, e.g., via a telephone line, for viewing, recording, or further processing.

Figure 3:
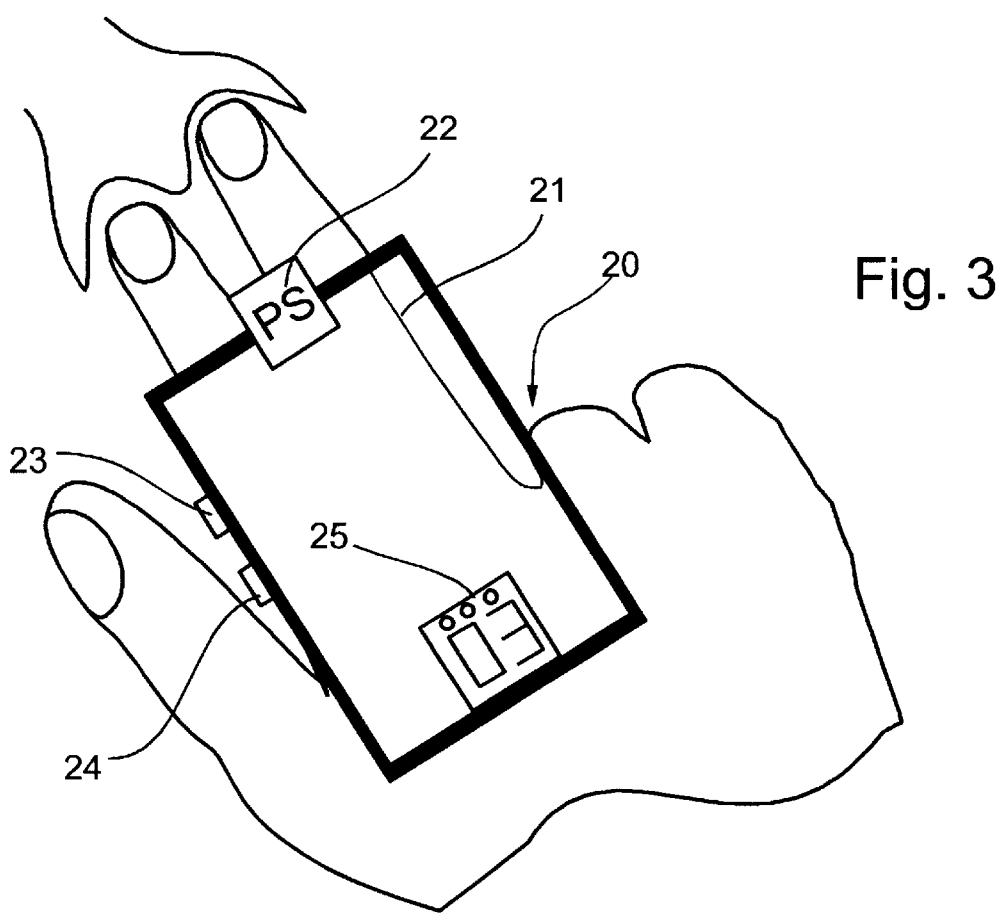
FIG. 3 illustrates a second form of probe constructed in accordance with the present invention.

FIG. 3 illustrates another construction of probe, therein generally designated 20, which may also be used. The probe 20 illustrated in FIG. 3 is directly mounted on at least one finger, and preferably on two fingers, of the user.

Thus, probe 20 illustrated in FIG. 3 includes a housing 21 mountable on two fingers (the index finger and the next adjacent finger) such as to expose the outer tips of the two fingers for direct contact with the spine (or other object whose contour is to be mapped). Housing 21 includes a position sensor 22 for sensing the instantaneous position of the probe in space, e.g., in the same manner as described above with respect to FIGS. 1 and 2. Probe 20 also includes a depressible button 23 for entering the instantaneous location of the position sensor, and a second depressible button 24 for clearing previous entries, in the same manner as described above with respect to probe 2 illustrated in FIG. 1.

Probe 20 in FIG. 3 may also include a display 25, which may be used for displaying each entry or any of the calculations produced by the workstation during an examination procedure. Such a display may also be included in probe 2 illustrated in FIG. 1; and similarly, probe 20 illustrated in FIG. 3 could also include an audible signal to indicate when an entry has been made, as in probe 2 illustrated in FIG. 1.

Figure 4:
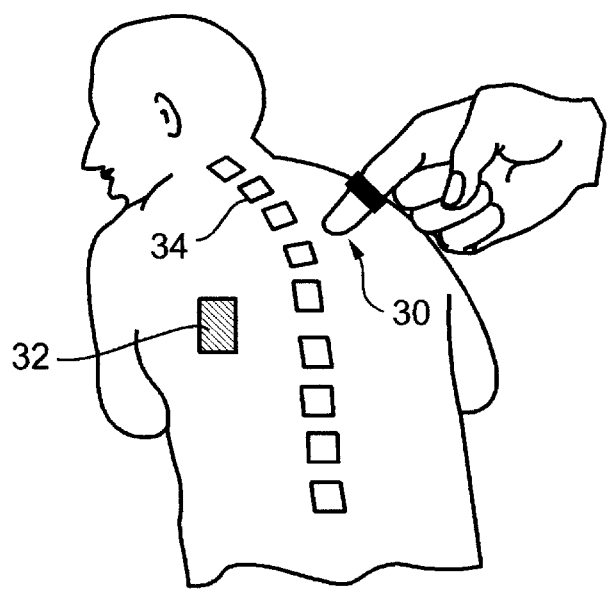
FIG. 4 illustrates a further embodiment of the invention wherein the system includes a reference position sensor (e.g., a magnetic field generator) fixed to the object (e.g., the back of the person whose spine is to be mapped), whereby the position tracking system tracks the movement of the position sensor with respect to that reference.

FIG. 4 illustrates a probe, therein generally designated 30, used with a reference sensor, generally designated 32, attached to the person's body at a fixed and known location with respect to a predetermined reference point of the spine 34. Thus, the position tracking system will track the movements of the probe 30 with respect to the reference 32; and since the position of the reference 32 is known with respect to the spine 34, the tracked movements of the probe trace the curvature of the spine. Such an arrangement makes the system sensitive only to the changes in position of the probe 30 with respect to the reference 32, and thereby enables the system to ignore changes in position of the person's body generally in space. The system illustrated in FIG. 4, therefore, is particularly useful for displaying the dynamic movements of the spine during body movements, e.g., forward and sideward bending movements.

Reference sensor 32 may be another position sensor which serves as a reference with respect to probe 30; alternatively, it may be the magnetic field generator itself which also thereby serves as a reference with respect to probe 30.

Figure 5:
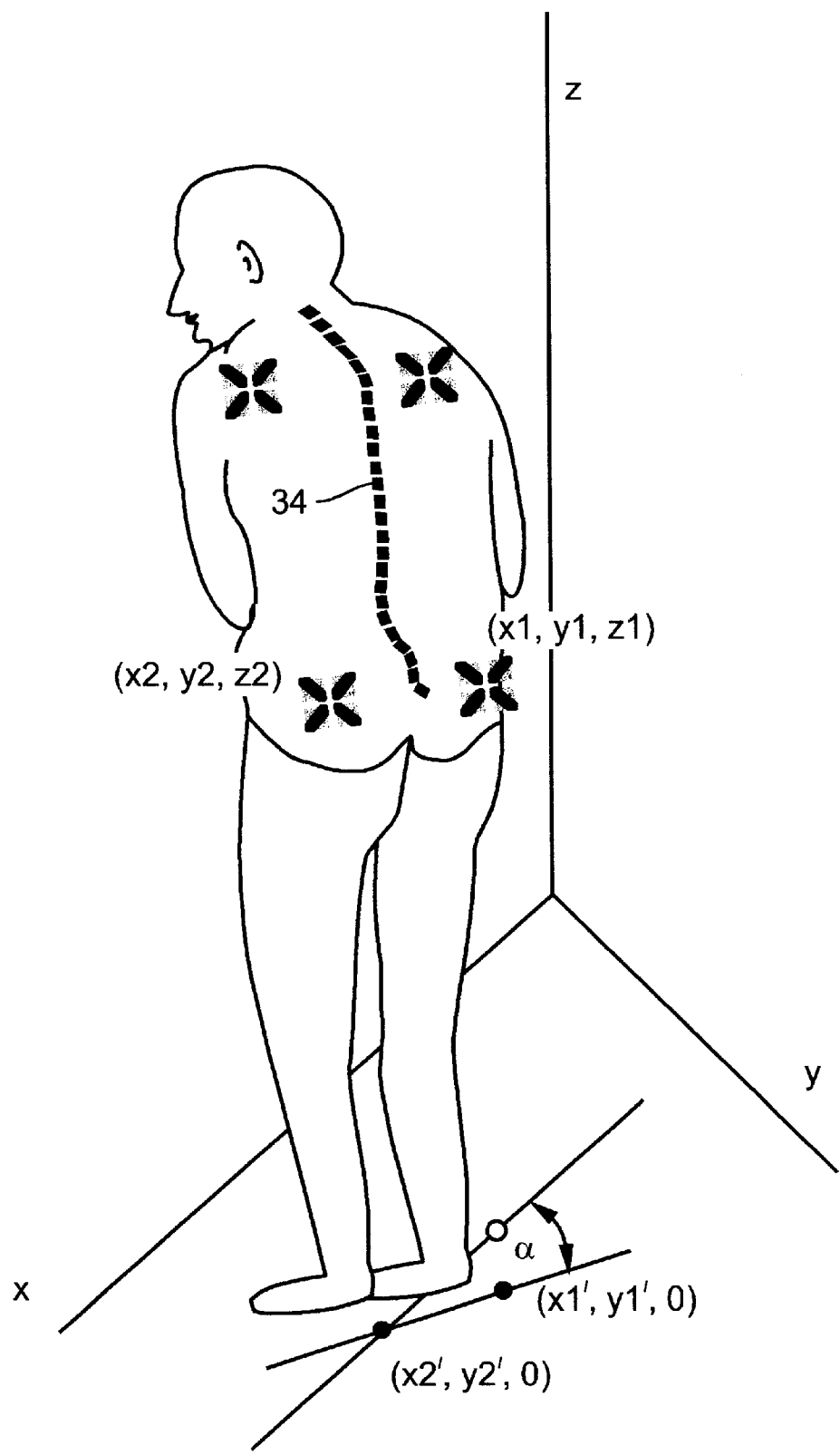
FIG. 5 is a diagram illustrating the manner of determining the spine coordinates using a coordinate-set generated by the field generator, and another coordinate-set defined by the subject.

FIG. 5 illustrates the manner in which the probe 30 of FIG. 4 may be used with a field generator used as the reference sensor 32 for mapping the curvature of the spine 34.

As shown in FIG. 5, two coordinate-sets are involved in acquiring the coordinates of the spine 34. One coordinate-set is generated by the field generator 32, and the second coordinate-set is defined according to the standing position of the subject. These two sets may not be correlated to each other for several reasons, e.g., the subject not standing exactly in the right coordinates of the generator, the generator not being perfectly parallel to the floor, etc. In order to provide accurate readings of each sensed spine position, a correction method is used to correct the deviation of the standing-position coordinates from the field-generator coordinates with respect to each measurement made in the standing position of the subject.

FIG. 5 illustrates the manner in which this is done with respect to one orthogonal plane, namely the (X,Y) plane. In the position illustrated in FIG. 5, the subject stands in a way that the posterior superior iliac spine coordinates (x1, y1, z1);(x2, y2, z2) are projected on the (X,Y) plane with a shift of $\alpha°$ in reference to the field-generator X-axis. A correction factor is thus calculated and applied to each actual reading made on the subject according to the standing-position coordinates of the subject.

Figure 6A:
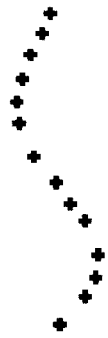
FIGS. 6a–6d illustrate the manner of utilizing the sampled points for producing a spine model.
Figure 6B:
Figure 6C:
Figure 6D:

FIGS. 6a–6d illustrate the manner of utilizing the sampled points for producing a calculated spine for the respective patient. FIG. 6a illustrates the sampled points; FIG. 6b illustrates the spine curve as generated by the sampled points, including interpolations between sample points; FIG. 6c illustrates the spine model produced with 18 points of the spine pattern with known vertebrae measurements and known distances from each other; and FIG. 6d illustrates the projection of the pattern of FIG. 6c on the interpolated spine of FIG. 6b.

After a set of points are sampled from the patient's spine, each point is characterized by the vector $(x,y,z,\alpha,\beta,\gamma)$, where $(x,y,z)$ are the coordinates, and $(\alpha,\beta,\gamma)$ are three angles in space. Where the goal is to build the curve as clinically accurate as possible to the patient's spine, the vectors of each vertebra are positioned in their right place over the calculated spine according to a spine-model, in a way that each vertebra is placed in the right distance from its neighbors and in the right angle in the spine (FIG. 6c). The model is built according to a known statistic scale of the spine and is used to normalize the samples and to scale them in the right proportion along the curve for angle calculations (FIG. 6d).

Figure 7:
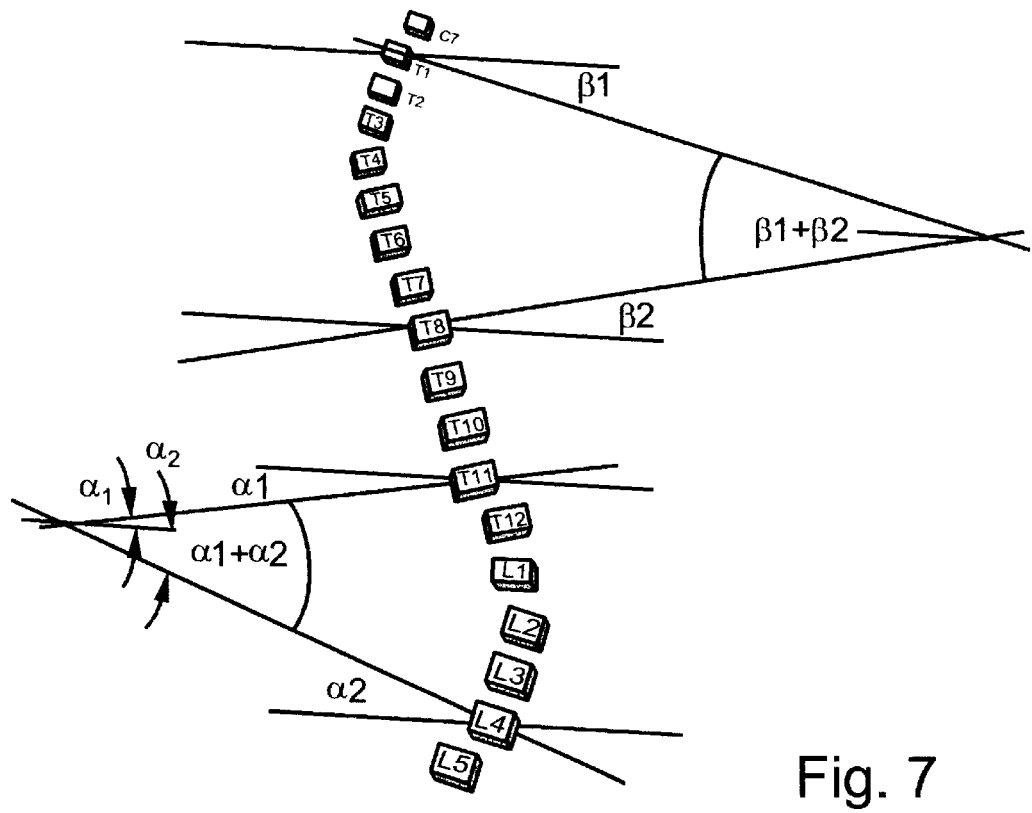
FIG. 7 is a view from the rear diagrammatically illustrating the manner of constructing the virtual spine out of the sampled points, scaling it to a model, and determining the curvature or deformity angles.

FIG. 7 illustrates the manner in which the spine model may be used for determining various characteristics of the vertebra, such as calculating the deformity or curvature angles. For this purpose, the vertebrae at the inflection points (points of direction change) are identified and their vertebra angles are calculated. For example, in the lower part of the S-curve illustrated in FIG. 7, the vertebrae at the inflection points are at T11 and L4, and the deformity angle of this curvature is $\alpha 1+\alpha 2$; whereas in the upper part of the S-curve, the vertebrae at the inflection points are $T_1$ and $T_8$, and the deformity angle is $\beta 1+\beta 2$.

It will be appreciated that each sampled point can be validated for legitimacy. Thus, since the overall structure of the spine is known, including the vertebrae place boundaries along the spine and the orientations of each vertebra in reference to its neighbors, it is possible to determine whether an actual reading is valid in relation to previous readings; if not, such a reading can be ignored.

At the present time, the physician uses a special ruler to calculate the deformity angle according to the known Cobb angle method. In this method, the physician manually draws the Cobb angle on the X-ray film from the vertebrae end plates. With the present invention, however, the Cobb angle may be reconstructed from the spinous process samples, as shown in FIG. 7.

Figure 8:
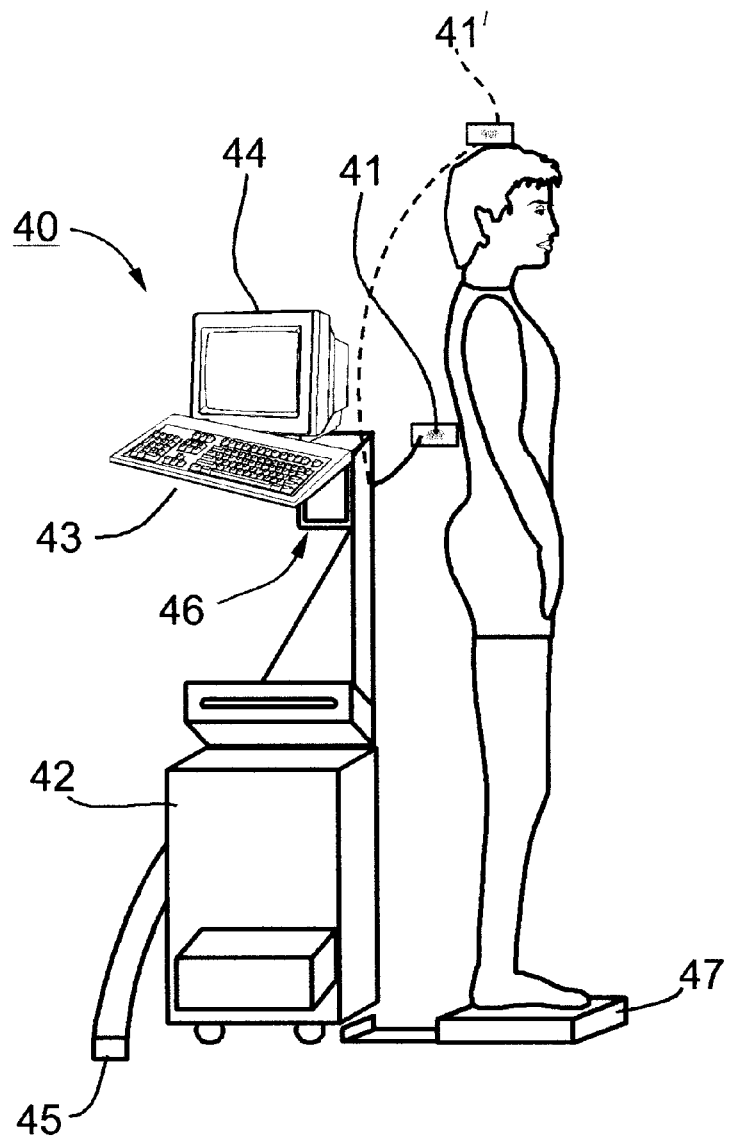
FIG. 8 pictorially illustrates a portable system constructed in accordance with the present invention.

FIG. 8 illustrates a system, generally designated 40, which may be constructed as a portable system for convenient transportation to various sites. The system illustrated in FIG. 8 includes a probe 41, which may be of any of the constructions described above, for application to the finger tip of the user to map the curvature of the subject's spine. The probe is connected to a workstation 42 which includes a user interface 43 and a display 44. The illustrated control system further includes a foot switch 45 which may be used for energizing the field generator 46, and/or for entering the readings, instead of, or in addition to, a control switch on the probe 41 itself.

As further shown in FIG. 8, the illustrated system also includes a scale 47 for weighing the patient and for entering the weight into the workstation 42. Other pertinent information may be entered into the workstation, for example the height of the patient as determined by placing the probe 41 at the top of the patient's head, as shown at 41', and determining the vertical position of the probe over the scale 47.

Figure 9:
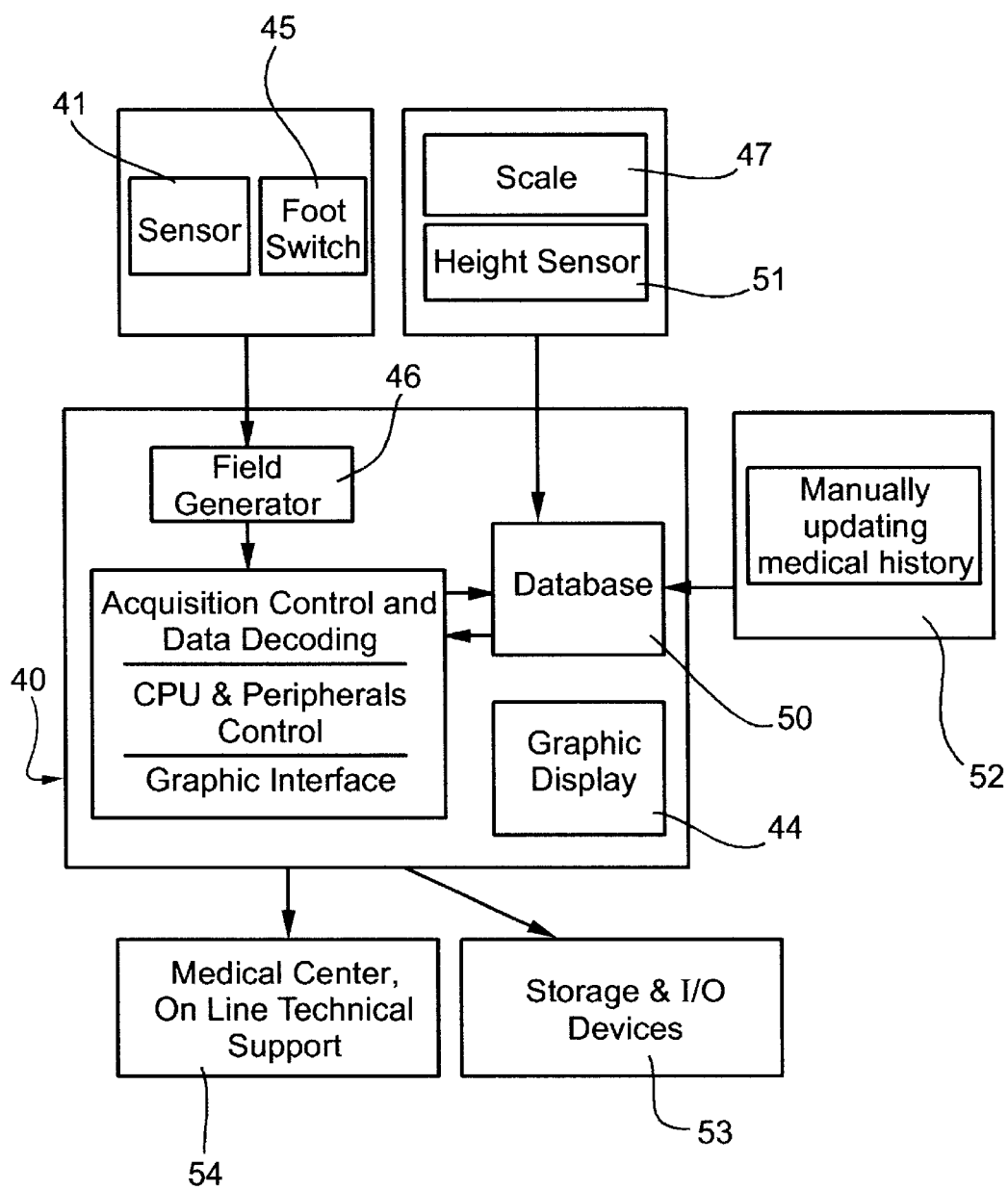
FIG. 9 is a block diagram illustrating the main components of the system of FIG. 8.

The overall electrical system is illustrated in the block diagram of FIG. 9. As shown in FIG. 9, the workstation 40 receives real-time control inputs from both the position sensor 41 and the field generator 46 as controlled by the foot-switch 45, and produces real-time feedback in order to track the movements of the position sensor, and thereby of the user's finger tips as they are moved along the vertebrae. The workstation 40 includes a database 50 for storing data during its processing, and a graphic display 44 for displaying the processed data. Communication with the database 50 is via a CPU and peripheral controls within the workstation 40, which includes the appropriate acquisition control and data decoding circuitry. Communication with the graphic display 44 is via graphic and video interface circuitry within the workstation 40. The workstation 40 receives, in addition to the data from the position sensor 41, also the weight data from the scale 47, and the height data 51 by reading the position of the position sensor 41 when placed at the top of the patient's head, as shown at 41' in FIG. 8.

The workstation 40 may also receive updating data, as shown at 52, for manually updating the medical history of the patient. The workstation 40 may also be connected to an external storage and input/output device, as shown at 53, for externally storing, displaying or processing the data. The workstation may also be connected to a telecommunication unit, as shown at 54, for transmitting the data to a remote location, such as a medical center or an on-line technical support facility.

The workstation 40 may process the inputted information according to the following algorithm:
(1) Read n points sampled from the patient's spine;
(2) "Copy" the constructed curve onto a spine model;
(3) Determine the position of each vertebra (XYZ axes and angles);
(4) Run a correction function (based on wide statistics researches) to convert the spinous process curve to the curve which passes through the middle of the vertebrae;
(5) Determine the vertebrae that define each curvature segment of the spine and calculate the deformity angle of such curvature segment.

Figure 10:
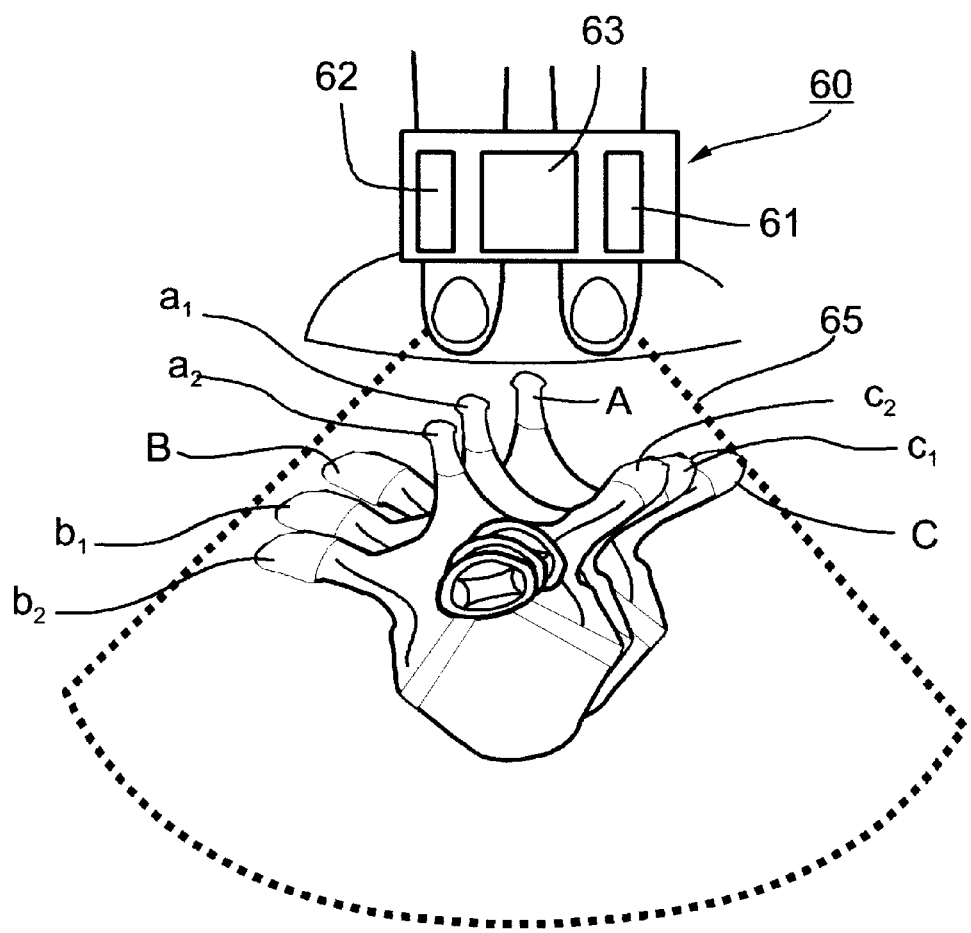
FIG. 10 illustrates a probe constructed in accordance with a further embodiment of the invention, including an ultrasound transducer with a position sensor, more particularly with two position sensors, and the manner in which such a probe is used for mapping the curvature of the spine and for analyzing the structure of selected vertebrae therein.

FIG. 10 illustrates a probe, generally designated 60, including a position sensor, in this case two position sensors 61, 62, and an ultrasonic transducer 63 located between the two position sensors. The ultrasonic transducer 63 senses or images the physical structure of particular vertebrae in the patient's spine (or other object whose contour is to be mapped) and displays this information or image, together with the position of the outer tip of the user's finger or fingers carrying the probe. The two position sensors 61, 62 thus sense and display the location of the surfaces touched by the finger tips, and thereby the locations of the vertebrae in the spinal column being analyzed; whereas the ultrasonic transducer 63 senses and displays the physical structure of the respective vertebra scanned, and displays information concerning such physical structure, particularly the location and contour of the two transverse processes relative to each other and to the spinous process of the examined vertebra, such as to provide an indication of the rotation and/or deformation of the respective vertebra.

The display 65 in FIG. 10 shows three vertebrae along the spine: The first one illustrates the normal position of the spinous process at "A", and the normal positions of the two transverse processes at "B" and "C", respectively. The next vertebra is rotated and the positions of its three processes are shifted due to an λ-degree of spine rotation as shown at $a_1$, $b_1$, $c_1$, respectively. The third vertebra is shifted even more such that its three processes are rotated to a more extreme degree as shown at $a_2$, $b_2$, $c_2$, respectively.

Figure 11:
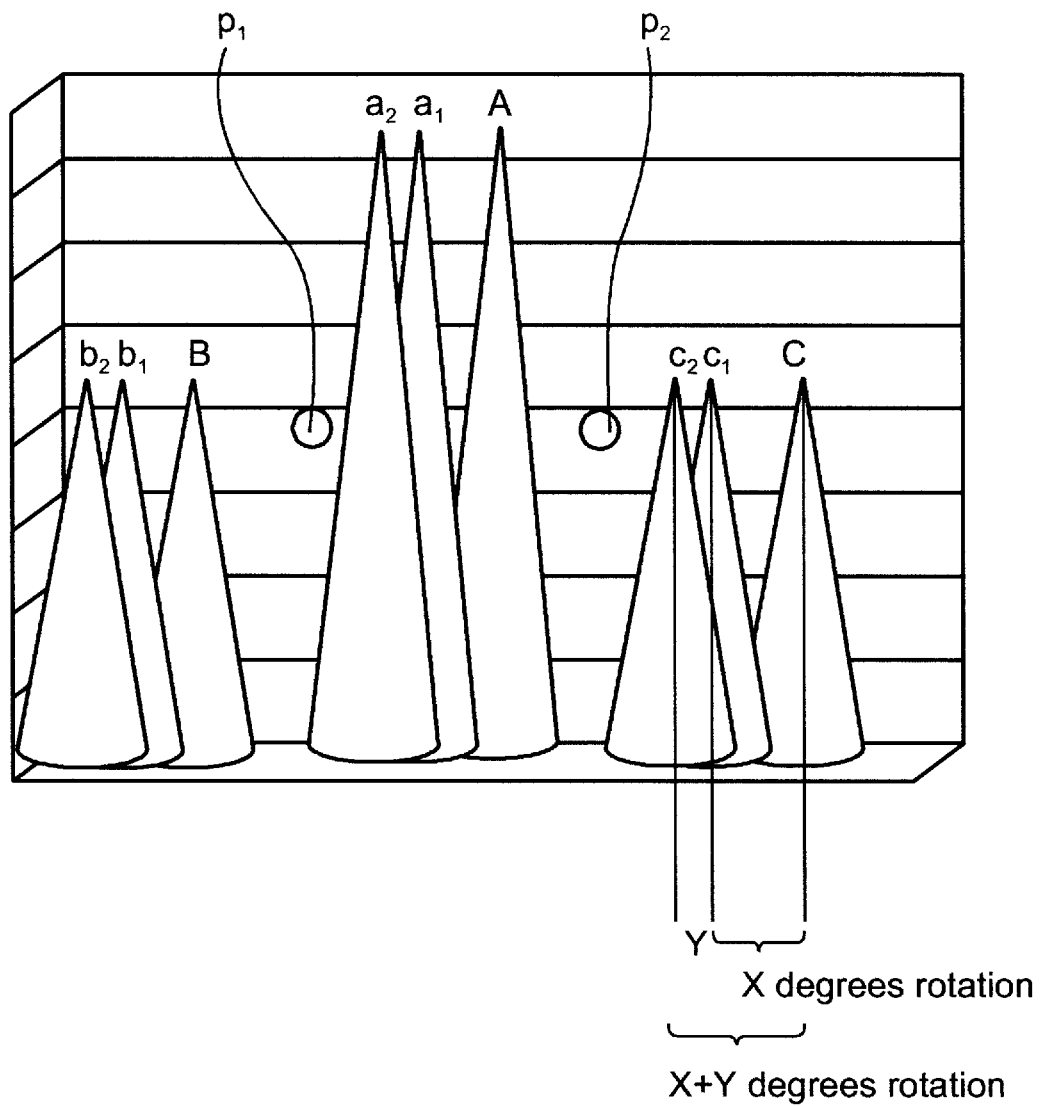
FIG. 11 graphically illustrates the manner in which the system of FIG. 10 may be used for indicating the degree of rotation of a vertebra due to spine deformity.

The graph of FIG. 11 illustrates the above conditions in the display 65, together with the displays of the two position sensors 61, 62, at $P_1$, $P_2$.

Figure 12:
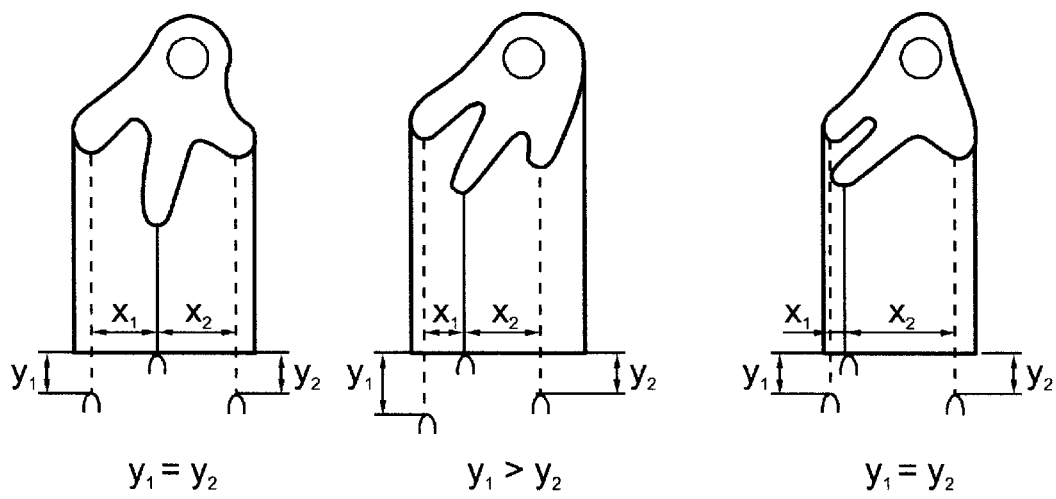
FIG. 12a illustrates the structure of a normal vertebra.
FIG. 12b illustrates the structure of a rotated vertebra.
FIG. 12c illustrates the structure of a deformed (but not rotated) vertebra.

FIGS. 12a–12c illustrate the images represented by the information produced by the ultrasonic transducer 63: Thus, FIG. 12a is for a normal vertebra; FIG. 12b is for a rotated vertebra; and FIG. 12c is for a deformed (not rotated) vertebra. In FIGS. 12a–12c, the values "$x_1$" and "$x_2$" represent the distance along the X-axis of the two transverse processes from the spineous process; and the values "$y_1$" and "$Y_2$" represent the distances of the two transverse processes from the spineous process along the Y-axis, i.e., toward the examiner's finger tip. It will be noted that in FIG. 12a, $x_1=x_2$, and $Y_1=Y_2$, thereby indicating a normal condition of the vertebra; in FIG. 12b, $x_1<x_2$ and $Y_1>Y_2$, thereby indicating a rotated condition of the vertebra; whereas in FIG. 12c, $x_1<x_2$ and $Y_1=Y_2$, thereby indicating a deformed (non-rotated) condition of the vertebra.

Figure 13:
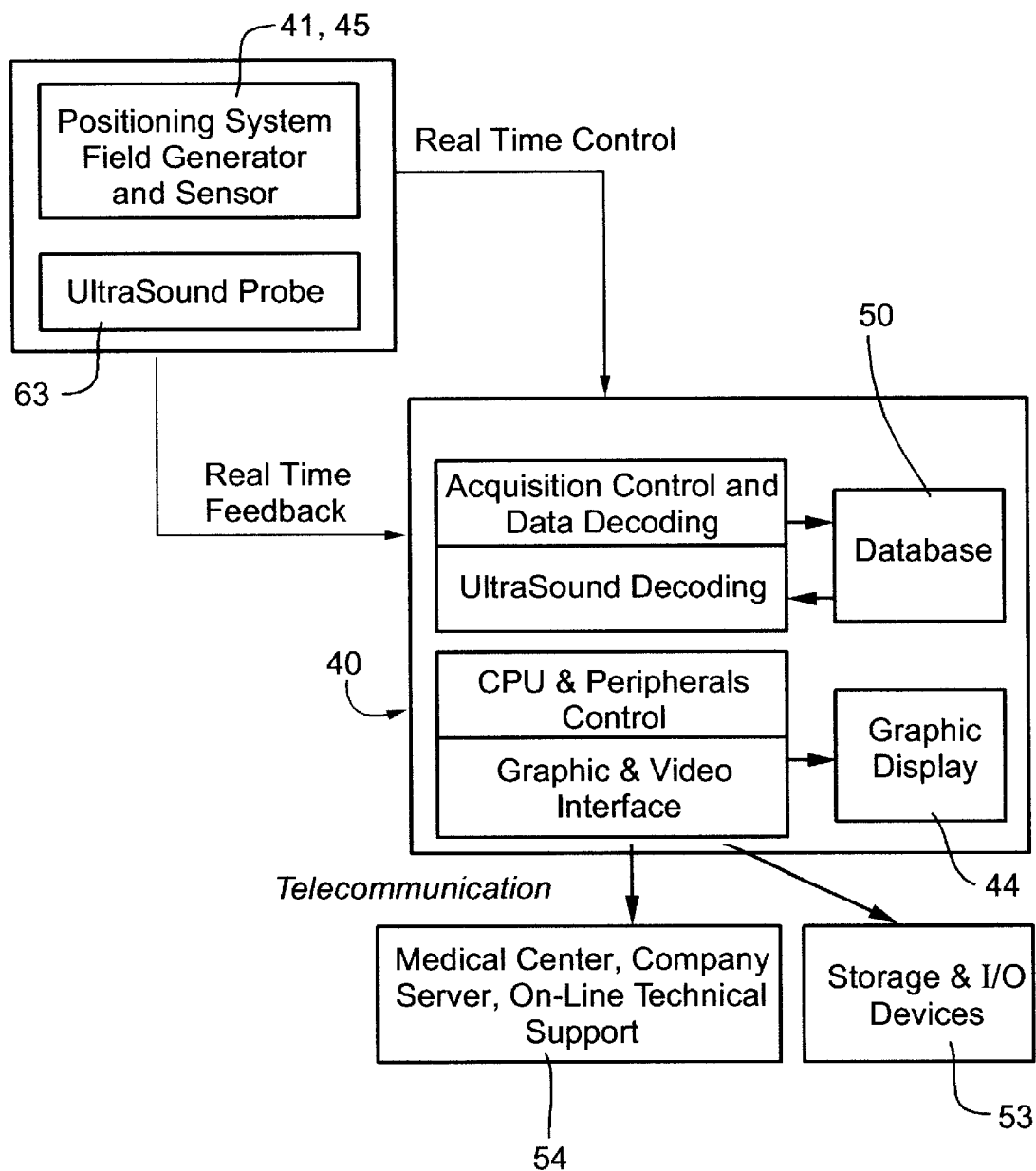
FIG. 13 is a block diagram illustrating the main components of a system using the probe of FIG. 10.

FIG. 13 illustrates the main components of the control system for the probe in FIG. 10. To facilitate understanding, those components which are generally the same as in FIG. 9 are identified by the same reference numerals. FIG. 13 shows the ultrasound transducer at 63.

Figure 14:
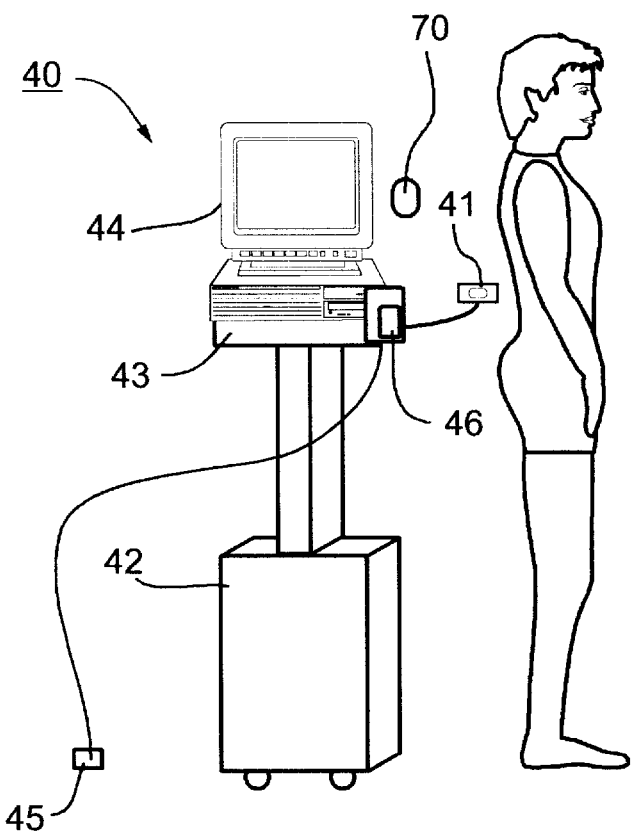
FIG. 14 is a pictorial illustration of another portable system using a separate ultrasound probe in addition to, or in lieu of, the finger tip probe.
Figure 15:
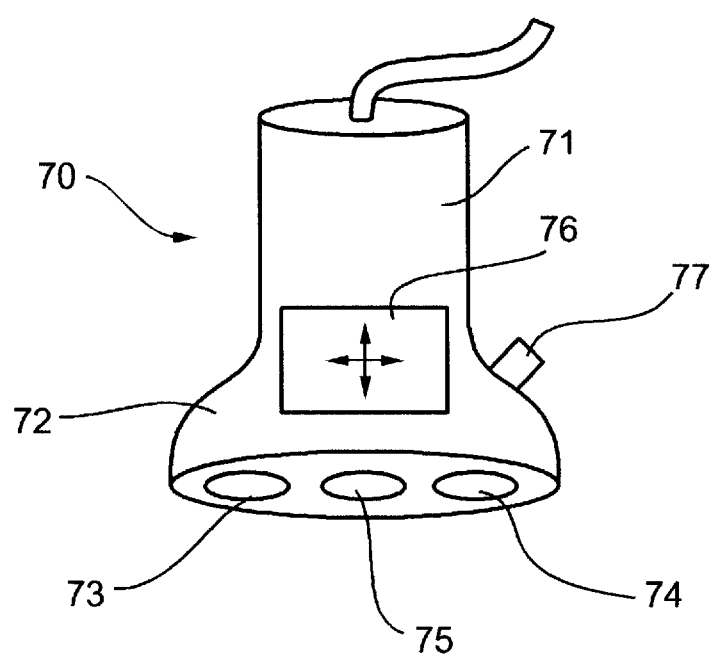
FIG. 15 illustrates an example of the separate ultrasound probe used in the system of FIG. 14.

FIGS. 14 and 15 illustrate a system similar to that of FIG. 8 but including, in addition to or in lieu of the finger probe 41, a display-type probe which includes the position sensor or sensors, an ultrasonic transducer, and also a display screen for navigating along the spine. The display-type probe shown in FIG. 14 is generally designated 70, and is more particularly illustrated in FIG. 15. The remainder of the system illustrated in FIG. 14 may otherwise be the same as described above with respect to FIG. 8, and therefore the same reference numerals have been used as in FIG. 8 to facilitate understanding.

With respect to the display-type probe 70 (as more particularly shown in FIG. 15), it includes a handle 71 graspable by the user, and a housing 72 enclosing within it a pair of position sensors 73, 74 (or only one position sensor), and an ultrasonic transducer 75 at one end of the housing to be placed against the spine of the patient being examined. The housing 72 further includes an LCD (liquid crystal display) screen 76 having arrows to direct the user to the right place and orientation of the probe with respect to the subject's spine. Housing 72 also includes a push-button 77 for entering the location of the position sensors.

Following is an example of how the probe 70 illustrated in FIGS. 14 and 15 may be used for making an examination;

1. The examiner wears the finger tip scanner 41 and palpates (feels) the spinous processes of the vertebrae in the patient's spine and enters the location and angle of each vertebra in the manner described above.
2. The system receives these entries, calculates the spinal curve, and finds the apex vertebrae (those at the inflection points) of each curvature segment, as described above with respect to FIG. 7.
3. The examiner then grasps the ultrasonic probe 70 and moves it along the spine of the patient to align it with each apex vertebra. Thus, since the system has previously calculated the location of each apex vertebra, and since the instantaneous location of the ultrasonic probe 70 can be determined by the positioning sensor 73, 74 on the probe 70 sensing the spinous processes of the vertebrae, the system can locate the instantaneous position of the probe with respect to a targeted apex vertebra and indicate the movements of the probe in order to align it with respect to a targetted apex vertebra. When the probe 70 exactly overlies a targetted apex vertebra, this is indicated by a validation light signal on the screen 76 of the probe.
4. The examiner, using the foot switch 45 or push-button 77, actuates the ultrasonic transducer 75 of the probe 70 to scan the respective apex vertebra and to display information regarding the physical structure of that vertebra, as described above particularly with respect to FIGS. 10–12, to thereby provide an indication of the rotation and/or deformation of the respective apex vertebra.
5. The system receives the ultrasonic signals from transducer 75, translates them into digital signals, and processes such signals to display the degree of rotation and/or deformation, if any, of the examined apex vertebra.

Specific Example of an Examining Procedure

Figure 16:
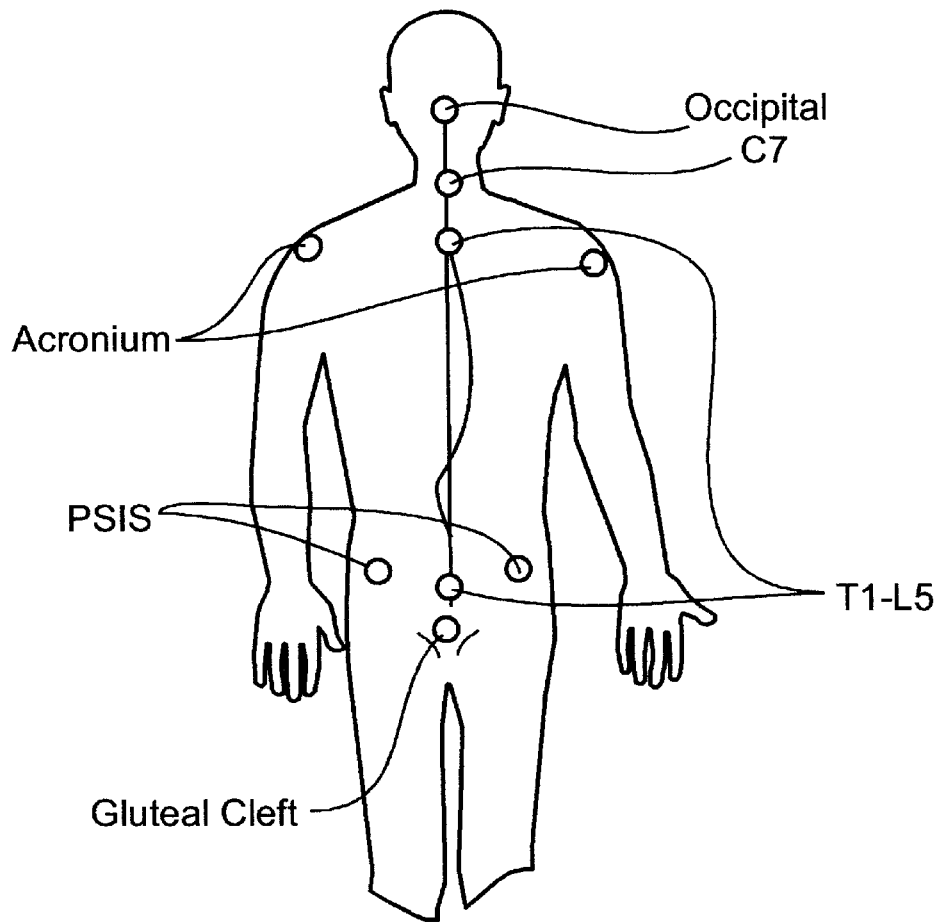
FIGS. 16 and 17 are diagrams helpful in explaining an example of a specific examining procedure using the system and probe of FIGS. 14 and 15, respectively.
Figure 17:
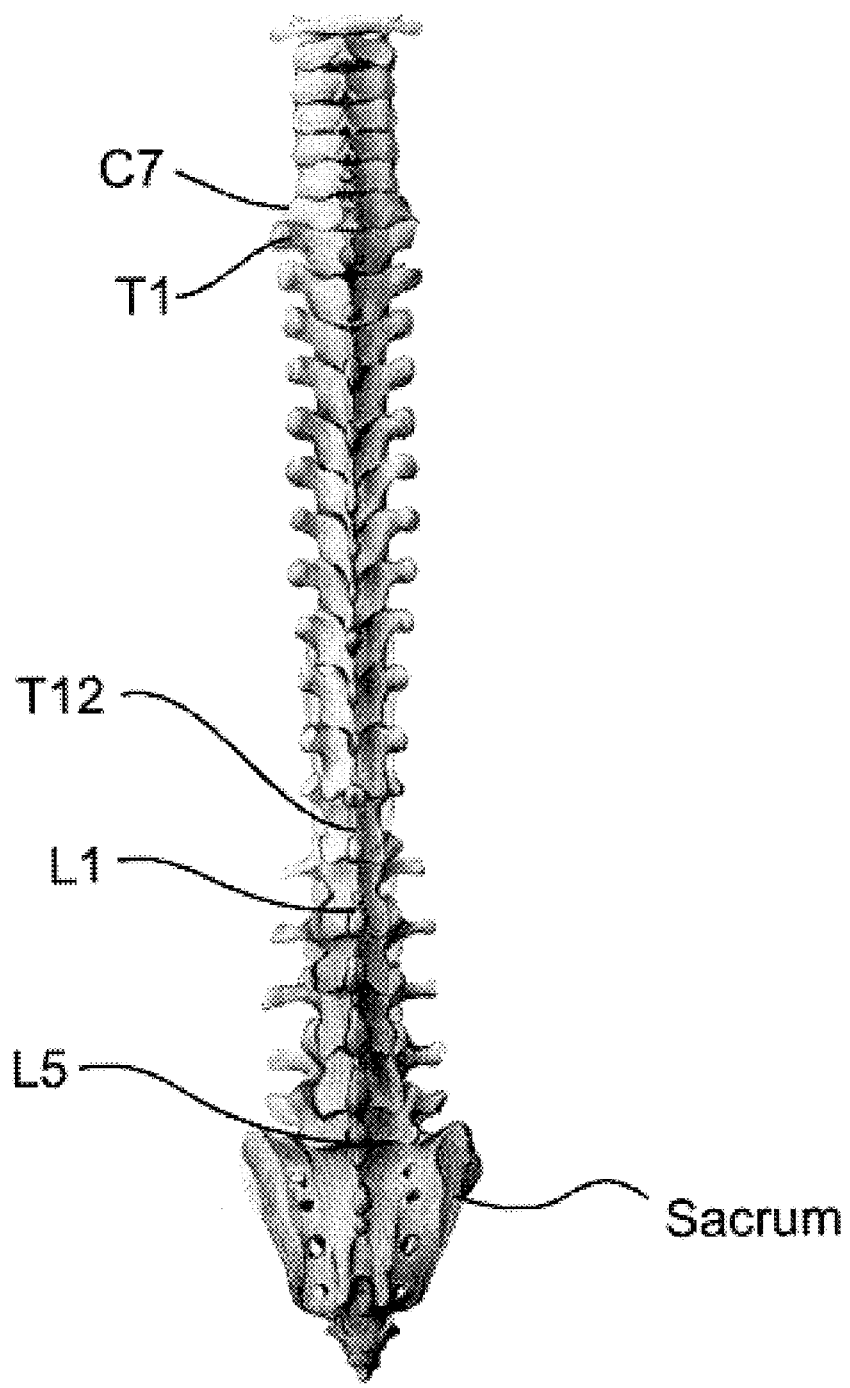

A specific example of an examining procedure will now be described with reference to FIGS. 16 and 17 and the algorithms illustrated by the flow chart of FIG. 18.

The inputs to the algorithm are coordinate samples, taken by conducting the examination twice on each patient. The readings required are the following (FIG. 16):

i). Vertebra C7—Reference point;
ii). Vertebrae T1–L5 (14 points out of 17 vertebras are needed);
iii). Superior border of the "Gluteal Cleft";
iv). 2 points of the PSIS (Posterior Superior Iliac Spine);
v). 2 points on the shoulders (Acronium);
vi). A point at the "Occipital Tuberance".

Real Time Points Identification and Validation

1. A Table Distance Test is performed wherein each vertebra is identified by the system according to built-in tables of distance (Z-axis) between vertebrae, based on statistics and literature. The coordinates (X, Y, Z) of the next digitized point have to fall within a certain range determined according to the above distance-tables. In order to get a full length of the spine, L5 (FIGS. 7, 17) must be digitized.

2. The "Gluteal Cleft" point (FIG. 16) is identified and validated by:
  i). a Z value lower than L5;
  ii). an X value approximately as L5;
3. The "PSIS" points are identified and validated by:
  i). a Z value for both points approximately the same.
  ii). An X value on two sides of L5.
  iii). A higher X value will identify the point as "Right PSIS"
  iv). A lower X value will identify the point as "Left PSIS"
4. The "Acronium" points are identified and validated by:
  i). a Z value of both points approximately the same.
  ii). an X value on two sides of C7, T1 (FIGS. 7, 17).
  iii). a higher X value will identify the point as "Right Shoulder".
  iv). a lower X value will identify the point as "Left Shoulder".
5. The "Occipital" point is identified and validated by:
  i). a Z value higher then C7.
  ii). an X value approximately as C7.

On Line Examination Quality Verification

Figure 18:
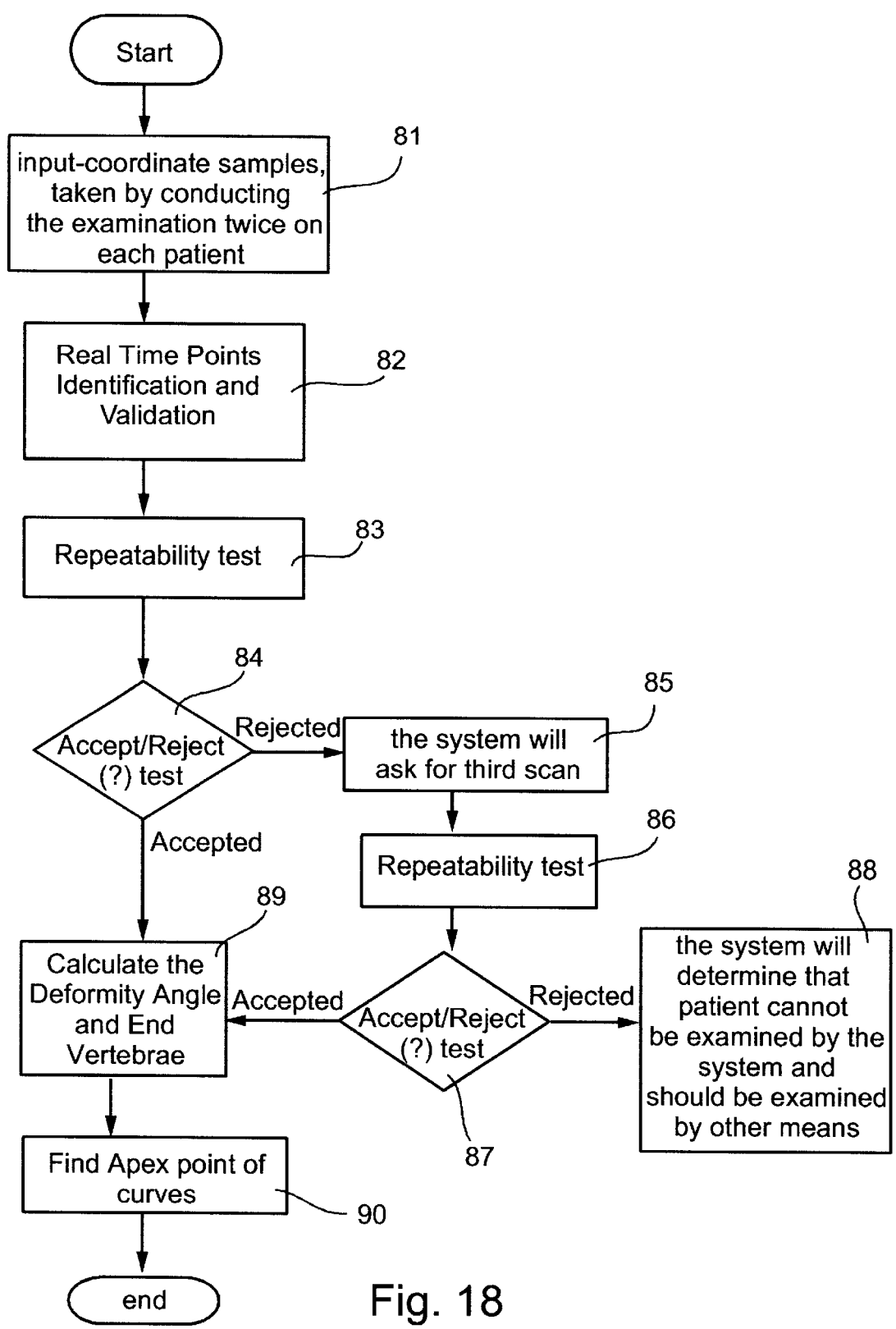
FIG. 18 is a flow chart illustrating the specific examining procedure of FIGS. 16 and 17.

In order to be certain that the examiner has accurately palpated the spinous processes, input coordinate samples are taken by conducting the examination twice on each patient and running a repeatability test on the two sets of points (blocks 81–83, FIG. 18). If rejected, the system asks for a third scan (scan 3), and a third repeatability test is performed (blocks 84, 85, 86). If again rejected, the system determines that the patient cannot be examined by the system, and should be examined by other means, e.g., X-ray, etc. (blocks 87, 88).

Where measurements are accepted, the system calculates the deformity angle and the end vertebrae (block 89), and finds the apex point of the curve (block 90).

The outputs according to the flow chart of FIG. 18 will therefore be:

(1.) the position coordinates for each vertebra;
(2.) the deformity angles;
(3.) the end vertebra for each angle; and
(4.) the apex vertebra for each angle.

It will thus be seen that the described system enables data representing, or relating to, the spine curvature to be obtained in a manner which is free of the health hazards characteristic of the presently-used X-ray equipment. The novel system allows frequent monitoring of the spinal curvature so as to permit a progressive analysis of the development of scoliosis or kyphosis based on consecutive scanning. If X-ray pictures have already been taken of the particular subject, the described system allows an augmented presentation of such X-ray pictures with the graphical presentation of the data acquired by the use of the equipment. The system also allows the measurement and display of many parameters of the patient's spine useful in analyzing its condition, such as the distance between vertebrae, the spine deformities or curvatures, and the degree of deformation or rotation of any selected vertebra, particularly the apex vertebrae of a curvature segment.

The described system further enables dynamic spine analysis (during bending), and limited space motion analysis (during movements). For example, the data processor may be programmed to display the dynamic movement of the spine while a point on the spine is contacted by the probe. Thus, the physician can touch a point on the spine, and while the patient is bending forwardly or sidewardly, e.g., at 90° (Adams test), at 45°, etc., data can be accumulated which can be integrated to simulate dynamical movements of the spine and indicate the degree of chest deformity and rotation.

The illustrated probes may utilize the user's finger to enter a position sensed by the probe into the position tracking system. In the above-described probes, the entry command is effected by depressing a push button and/or by a foot pedal, but other arrangements could be used. For example, the entry command could be effected by an electrical switch which is actuated by contact of the probe or the user's finger with the object, (e.g., the person's spine) to be mapped, or which is actuated by a proximity detector when at a predetermined proximity from the object. The entry command could also be effected by a voice-responsive device. The use of a probe, such as shown at 70 in FIGS. 14 and 15, which includes a screen having arrows, etc., directs the user to the right location and orientation for the ultrasonic transducer 75.

In addition, the data may be entered continuously to map the spinal column or other object. Alternatively, the data may be entered in the form of selected samples, which samples could be used, by either interpolation or extrapolation, for deriving any desired information regarding the spinal column or other object being mapped.

While the preferred embodiments described above utilize an electromagnetic-field position tracking system for tracking the movements of the probe, other forms of position tracking systems could be used, such as optical systems, sonic systems, articulated arm systems, infrared systems, and other such systems well known in the art.

Therefore, while the invention has been described with respect to several preferred embodiments, it will be appreciated that these are set forth merely for purposes of example, and that many other variations, modifications and applications of the invention may be made.

What is claimed is:

1. A probe for use in a contour mapping system, said probe being constructed so as to be carried by a user's hand with a finger tip of at least one finger of the user's hand movable along the outer surface of the object whose contour is to be mapped; said probe including a position sensor to be located at a predetermined position with respect to said finger tip for sensing the position of the probe, and thereby of said finger tip, as the probe is moved by the user's hand along the outer surface of the object whose contour is to be mapped.

2. The probe according to claim 1, wherein said probe further comprises a depressible button depressible by the thumb of the user's hand to enter the location of said position sensor at the instant the button is depressed.

3. The probe according to claim 1, wherein said probe is constructed for grasping by the user's hand with the finger tip of at least one finger in said predetermined position with respect to said position sensor of the probe.

4. The probe according to claim 1, wherein said probe includes a handle graspable by the user's hand, and a finger supporting member fixed at one end of said handle for supporting the user's index finger tip at said predetermined position with respect to the position sensor of the probe.

5. The probe according to claim 4, wherein said position sensor is fixed within said finger supporting member.

6. The probe according to claim 1, wherein said probe is constructed for mounting on said at least one finger of the user's hand, with said position sensor at said predetermined position with respect to said finger tip.

7. The probe according to claim 6, wherein said probe is constructed so as to expose said finger tip for direct contact with the outer surface of the object whose contour is to be mapped.

8. The probe according to claim 1, wherein said probe is constructed for mounting on two adjacent fingers of the user's hand with the tips of the two adjacent fingers exposed for direct contact with the object whose contour is to be mapped.

9. The probe according to claim 1, wherein said probe also includes an ultrasonic transducer for sensing the physical structure of the object whose contour is to be mapped.

10. The probe according to claim 9, wherein said probe includes two position sensors located on opposite sides of said ultrasonic transducer.

11. A probe for contour mapping the outer surface of an object comprising: a position sensor carried by the probe for sensing the position of the probe as it is moved along the outer surface of the object whose contour is to be mapped; and an ultrasonic transducer carried by the probe for sensing the physical structure of the object whose contour is to be mapped.

12. The probe according to claim 11, wherein the probe also includes a display screen for displaying the movements of the probe as it is moved along the outer surface of the object.

13. The probe according to claim 11, wherein the probe includes two position sensors on opposite sides of the ultrasonic transducer.

14. The probe according to claim 11, wherein the probe further includes a handle for grasping the probe and for moving it along the outer surface of the object.

15. A contour mapping system for mapping the contour of an object, comprising: a probe according to claim 1; and a position tracking system for tracking the movements of the position sensor of the probe, and thereby of the finger tip of the user's hand, as the probe is moved with the user's hand along the outer surface of said object.

16. The system according to claim 15, wherein said position tracking system includes a magnetic field generator for generating a magnetic field in the space occupied by said object, and the position sensor of the probe is a magnetic sensor for sensing the instantaneous position of the probe within said magnetic field.

17. The system according to claim 15, wherein said position tracking system is included in a workstation which further includes a data processor and a display for displaying data corresponding to the instantaneous position of the probe as it is moved along the outer surface of the object.

18. The system according to claim 17, wherein said data processor further includes a storage device for storing said displayed data in a manner enabling it to be retrieved for comparison with corresponding data obtained by subsequently mapping said object.

19. The system according to claim 17, wherein said system further comprises a reference fixed to said object, and said position tracking system tracks the movements of said position sensor with respect to said reference.

20. The system according to claim 17, wherein said probe also includes an ultrasonic transducer for sensing the physical structure of said object; and wherein said system further includes a display for displaying the position of said probe position sensor, and thereby of the outer tip of said at least one finger, together with information representing the physical structure of said object.

21. The system according to claim 20, wherein said probe includes two position sensors located on opposite sides of said ultrasonic transducer, said display displaying the physical structure of said object together with the positions of said two position sensors.

22. The system according to claim 17, wherein the object whose contour is to be mapped is the spine of a person, and said data processor is programmed to display data regarding the person's spine as mapped by said probe.

23. The system according to claim 22, wherein the system further includes a weighing scale for measuring the weight of the person and for displaying the measured weight on the display.

24. A contour mapping system for mapping the contour of an object, comprising: a probe according to claim 11; a position tracking system for tracking the movements of the position sensor as the probe is moved along the outer surface of the object; and a display screen for displaying the movements of the probe as the probe is moved along the outer surface of the object, and the physical structure of the object at any selected location thereon.

25. The system according to claim 24, wherein the object whose contour is to be mapped is the spine of a person, and said data processor is programmed to display data regarding the person's spine as mapped by said probe.

26. A method of examining a subject's spine, comprising:
providing the hand of an examiner with a probe having a position sensor at a predetermined location with respect to a finger tip of the examiner's hand;
moving the finger tip along the spinous processes of the vertebrae of the subject's spine;
upon feeling a spinous process with the finger tip, recording the position of the probe, and thereby of the felt spinous process;
and utilizing said recorded positions of the felt spinous processes to calculate and display the curvature of the subject's spine.

27. The method according to claim 26, wherein the location and angle of each vertebra is determined, the curvature of the spine is calculated, and the deformity angle of at least one segment of the spine defined by two inflection points is determined by the deformity angles of the two vertebrae at the inflection points defining the respective segment.

28. The method according to claim 26, wherein the examiner's finger tip is moved to the top of the subject's head, and the position of the probe is recorded to also provide a measurement of the subject's height.

29. The method according to claim 26, wherein at least one vertebra in the subject's spine is examined for rotation and/or deformation.

30. The method according to claim 29, wherein said examined vertebra is examined by an ultrasonic transducer carried by said probe and producing a display of information regarding the physical structure of said vertebra.

31. The method according to claim 30, wherein said examined vertebra is an apex vertebra at an inflection point in the curvature of the subject's spine.

32. The method according to claim 30, wherein said displayed information includes information as to the location and contour of the two transverse processes relative to each other and to the spinous process of said apex vertebra such as to provide an indication of the rotation and/or deformation of the examined apex vertebra.

33. A method of examining a subject's spine, comprising:
moving a position sensor along the outer surface of the subject's spine to map the subject's spine curvature;
and utilizing an ultrasonic transducer to examine the physical structure of at least one vertebra of the subject's spine to detect deformation and/or rotation of the examined vertebra.

34. The method according to claim 33, wherein said position sensor and said ultrasonic transducer are both carried by the same probe.

35. The method according to claim 33, wherein said at least one vertebra examined is an apex vertebra at an inflection point of the subject's spine curvature.

36. The method according to claim 33, wherein said position sensor maps the subject's spine curvature by sensing the spinous processes of the vertebrae in the subject's spine; and said ultrasonic transducer examines the physical structure of at least one vertebra by sensing and displaying the location and contour of the two transverse processes relative to each other and to the spinous process of the examined vertebra such as to provide an indication of the rotation and/or deformation of the examined vertebra.

37. The method according to claim 36, wherein the location and angle of each vertebra is determined, the curvature of the spine is calculated, and the deformity angle of at least one segment of the spine defined by two inflection points is determined by the deformity angles of the two vertebrae at the inflection points defining the respective segment.

38. The method according to claim 33, wherein said position sensor and said ultrasonic transducer are both on a probe carried by a hand of an examiner examining said subject's spine.

39. The method according to claim 38, wherein said probe is carried by the examiner's hand such that said position sensor is at a predetermined location with respect to a finger tip of the examiner's hand, and the examiner's finger tip is moved along the spinous processes of the subject's spine to map the curvature of the subject's spine.

40. The method according to claim 39, wherein said ultrasonic transducer is utilized to display the location of the two transverse processes relative to each other and to the spinous process of said examined vertebra such as to provide an indication of the rotation and/or deformation of the examined vertebra.

* * * * *